(12) United States Patent
Stern et al.

(10) Patent No.: US 6,391,633 B1
(45) Date of Patent: May 21, 2002

(54) PRODUCTION OF ERYTHROPOIETIN BY ENDOGENOUS GENE ACTIVATION

(75) Inventors: Anne Stern, Penzberg; Michael Brandt, Iffeldorf; Konrad Honold; Johannes Auer, both of Penzberg; Hans Koll, Weilheim, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/463,380

(22) PCT Filed: Jul. 22, 1998

(86) PCT No.: PCT/EP98/04590

§ 371 Date: Jan. 21, 2000

§ 102(e) Date: Jan. 21, 2000

(87) PCT Pub. No.: WO99/05268

PCT Pub. Date: Feb. 4, 1999

(30) Foreign Application Priority Data

Jul. 23, 1997 (EP) .............................. 97112640
Dec. 3, 1997 (DE) .......................... 197 53 681

(51) Int. Cl.$^7$ .............................. C12N 5/06; C12N 5/16; C12P 21/04
(52) U.S. Cl. .................. 435/335; 435/70.1; 930/90
(58) Field of Search ............................ 435/69.1, 70.1, 435/335; 530/412; 930/90

(56) References Cited

U.S. PATENT DOCUMENTS 4,923,808 A * 5/1990 Matteucci .................. 435/69.8
5,981,214 A * 11/1999 Skoultchi

FOREIGN PATENT DOCUMENTS

| EP | 0232034 | 8/1987 |
|---|---|---|
| EP | 0267678 | 5/1988 |
| EP | 0411678 | 2/1991 |
| EP | 0747485 | 12/1996 |
| EP | 0747485 A1 * | 12/1996 |
| WO | 9109955 | 7/1991 |
| WO | 9309222 | 5/1993 |
| WO | 9412650 | 6/1994 |
| WO | 9531560 | 11/1995 |
| WO | WO 9531560 * | 11/1995 |
| WO | 9619573 | 6/1996 |
| WO | 9629411 | 9/1996 |

OTHER PUBLICATIONS

Yanagi et al. 1989. DNA. 8:419–427.*
Stellwagen. 1990. in Deutscher, ed. Methods in Enzymology vol. 182, pp. 317–328.*
Mather. 1990. in Goeddel et al., eds. Methods in Enzymology vol. 185, pp. 572 and 576.*
Sambrook et al. 1989. Molecular Cloning. cold Spring Harbor Laboratory Press. p. 16.30.*
Simonsen et al. 1983. Proc. Natl. Acad. Sci. USA. 80:2495–2499.*
Recny et al., *Journal of Biological Chemistry*, 262:35:17156–17163 (Dec. 15, 1987).
Krystal et al., *Blood*, 67:1:71–79 (Jan. 1986).
Simonsen et al., *Proceedings of the National Academy of Sciences of USA*, 80:2495–2499 (May 1983).

* cited by examiner

*Primary Examiner*—Remy Yucel
(74) *Attorney, Agent, or Firm*—Fulbright & Jaworski, LLP

(57) ABSTRACT

The invention relates to human cells which are capable, on the basis of an activation of the endogenous human EPO gene, of producing EPO in a sufficient amount and purity to make possible a cost-effective production of human EPO as a pharmaceutical preparation. The invention furthermore relates to a method for the preparation of such human EPO-producing cells, DNA constructs for the activation of the endogenous EPO inhuman cells, and a method for the large technical production of EPO in human cells.

22 Claims, 9 Drawing Sheets

Gene Activation Sequence

SEQUENCE LISTING

<160> NUMBER OF SEQ ID NOS: 17

<210> SEQ ID NO 1
<211> LENGTH: 32
<212> TYPE: DNA
<213> ORGANISM: Artificial Sequence
<220> FEATURE:
<223> OTHER INFORMATION: Nucleotide sequence of the primer used for
      preparing PCR Product 1

<400> SEQUENCE: 1
cgcggcggat cccagggagc tgggttgacc gg                              32

<210> SEQ ID NO 2
<211> LENGTH: 38
<212> TYPE: DNA
<213> ORGANISM: Artificial Sequence
<220> FEATURE:
<223> OTHER INFORMATION: Nucleotide sequence of the primer used for
      preparing PCR Product 1

<400> SEQUENCE: 2
ggccgcgaat tctccgcgcc tggccggggt ccctcagc                        38

<210> SEQ ID NO 3
<211> LENGTH: 36
<212> TYPE: DNA
<213> ORGANISM: Artificial Sequence
<220> FEATURE:
<223> OTHER INFORMATION: Nucleotide sequence of the primer used for
      preparing PCR Product 2

<400> SEQUENCE: 3
cgcggcggat cctctcctcc ctcccaagct gcaatc                          36

<210> SEQ ID NO 4
<211> LENGTH: 36
<212> TYPE: DNA
<213> ORGANISM: Artificial sequence
<220> FEATURE:
<223> OTHER INFORMATION: Nucleotide sequence of the primer used for
      preparing PCR Product 2

<400> SEQUENCE: 4
ggccgcgaat tctagaacag atagccaggc tgagag                          36

<210> SEQ ID NO 5
<211> LENGTH: 24
<212> TYPE: DNA
<213> ORGANISM: Artificial Sequence
<220> FEATURE:
<223> OTHER INFORMATION: Nucleotide sequence of the primer EPO EX1

<400> SEQUENCE: 5
tcacccggcg cgccccaggt cgct                                       24

<210> SEQ ID NO 6
<211> LENGTH: 61
<212> TYPE: DNA
<213> ORGANISM: Artificial Sequence
<220> FEATURE:
<223> OTHER INFORMATION: Nucleotide sequence of the primer EX2

<400> SEQUENCE: 6
atgctcgagc ggccgccagt gtgatggata tctgcagagc tcagcttggc c gcgaattct    60

```
a                                                              61
```

```
<210> SEQ ID NO 7
<211> LENGTH: 78
<212> TYPE: DNA
<213> ORGANISM: Artificial sequence
<220> FEATURE:
<221> NAME/KEY: CDS
<222> LOCATION: 49..60
<223> OTHER INFORMATION: Nucleotide sequence of the primer EX3
                        (Met-Gly-Ala-His),

<400> SEQUENCE: 7
tcacccggcg cgccccaggt cgctgaggga ccccggccag gcgcggag atg  ggg gcc    57
                                                     Met  Gly Ala cac ggtgagtact cgcgggct                                             78
His
```

```
<210> SEQ ID NO 8
<211> LENGTH: 4
<212> TYPE: Protein
<213> ORGANISM: Artificial Sequence
<220> FEATURE:
<223> OTHER INFORMATION: Amino acid sequence of the modified signal
                        peptide start coded by primer EX3

<400> SEQUENCE: 8

Met Gly Ala His
```

```
<210> SEQ ID NO 9
<211> LENGTH: 78
<212> TYPE: DNA
<213> ORGANISM: Artificial Sequence
<220> FEATURE:
<221> NAME/KEY: CDS
<222> LOCATION: 49..60
<223> OTHER INFORMATION: Nucleotide sequence of primer EX4
                        (Met-Ser-Ala-His)

<400> SEQUENCE: 9
tcacccggcg cgccccaggt cgctgaggga ccccggccag gcgcggag atg  agc gcc    57
                                                     Met  Ser Ala cac ggtgagtact cgcgggct                                             78
His
```

```
<210> SEQ ID NO 10
<211> LENGTH: 4
<212> TYPE: Protein
<213> ORGANISM: Artificial Sequence
<220> FEATURE:
<223> OTHER INFORMATION: Amino acid sequence of the modified signal
                        peptide start coded by primer EX4

<400> SEQUENCE: 10

Met Ser Ala His
```

```
<210> SEQ ID NO 11
<211> LENGTH: 78
<212> TYPE: DNA
<213> ORGANISM: Artificial Sequence
<220> FEATURE:
<221> NAME/KEY: CDS
<222> LOCATION: 49.. 60
<223> OTHER INFORMATION: Nucleotide sequence of primer EX5
                        (Met-Gly-Val-Pro)

<400> SEQUENCE: 11
```

```
tcacccggcg cgccccaggt cgctgaggga ccccggccag gcgcgg ag atg ggg gtg      57
                                                      Met Gly Val ccc ggtgagtact cgcgggct                                                78
Pro
```

<210> SEQ ID NO 12
<211> LENGTH: 4
<212> TYPE: Protein
<213> ORGANISM: Artificial sequence
<220> FEATURE:
<223> OTHER INFORMATION: Amino acid sequence of the modified signal
       peptide start coded by primer EX5

<400> SEQUENCE: 12

Met Gly Val Pro

<210> SEQ ID NO 13
<211> LENGTH: 78
<212> TYPE: DNA
<213> ORGANISM: Artificial sequence
<220> FEATURE:
<221> NAME/KEY: CDS
<222> LOCATION: 49 . . 60
<223> OTHER INFORMATION: Nucleotide sequence of primer EX6
       (Met-Ser-Val-His)

<400> SEQUENCE: 13

```
tcacccggcg cgccccaggt cgctgaggga ccccggccag gcgcggag atg  agc gtg      57
                                                     Met  Ser Val cac ggtgagtact cgcgggct                                                78
His
```

<210> SEQ ID NO 14
<211> LENGTH: 4
<212> TYPE: Protein
<213> ORGANISM: Artificial Sequence
<220> FEATURE:
<223> OTHER INFORMATION: Amino acid sequence of the modified signal
       peptide start coded by primer EX6

<400> SEQUENCE: 14

Met Ser Val His

<210> SEQ ID NO 15
<211> LENGTH: 59
<212> TYPE: DNA
<213> ORGANISM: Artificial Sequence
<220> FEATURE:
<223> OTHER INFORMATION: Nucleotide sequence of primer EX genome 1

<400> SEQUENCE: 15

```
ggacattcta gaacagatat ccaggctgag cgtcaggcgg ggagggagaa g ggtggctg      59
```

<210> SEQ ID NO 16
<211> LENGTH: 48
<212> TYPE: DNA
<213> ORGANISM: Artificial Sequence
<220> FEATURE:
<223> OTHER INFORMATION: Nucleotide sequence of primer EX13

<400> SEQUENCE: 16

```
gtgatggata tctctagaac agatagccag gctgagagtc aggcgggg                   48
```

<210> SEQ ID NO 17
<211> LENGTH: 39

-continued

```
<212> TYPE: DNA
<213> ORGANISM: Artificial Sequence
<220> FEATURE:
<223> OTHER INFORMATION: Nucleotide sequence of primer EPO EX 17

<400> SEQUENCE: 17
atggatatca tcgattctag aacagatagc caggctgag                                    39
```

PRODUCTION OF ERYTHROPOIETIN BY ENDOGENOUS GENE ACTIVATION

RELATED APPLICATIONS

Figure 1:
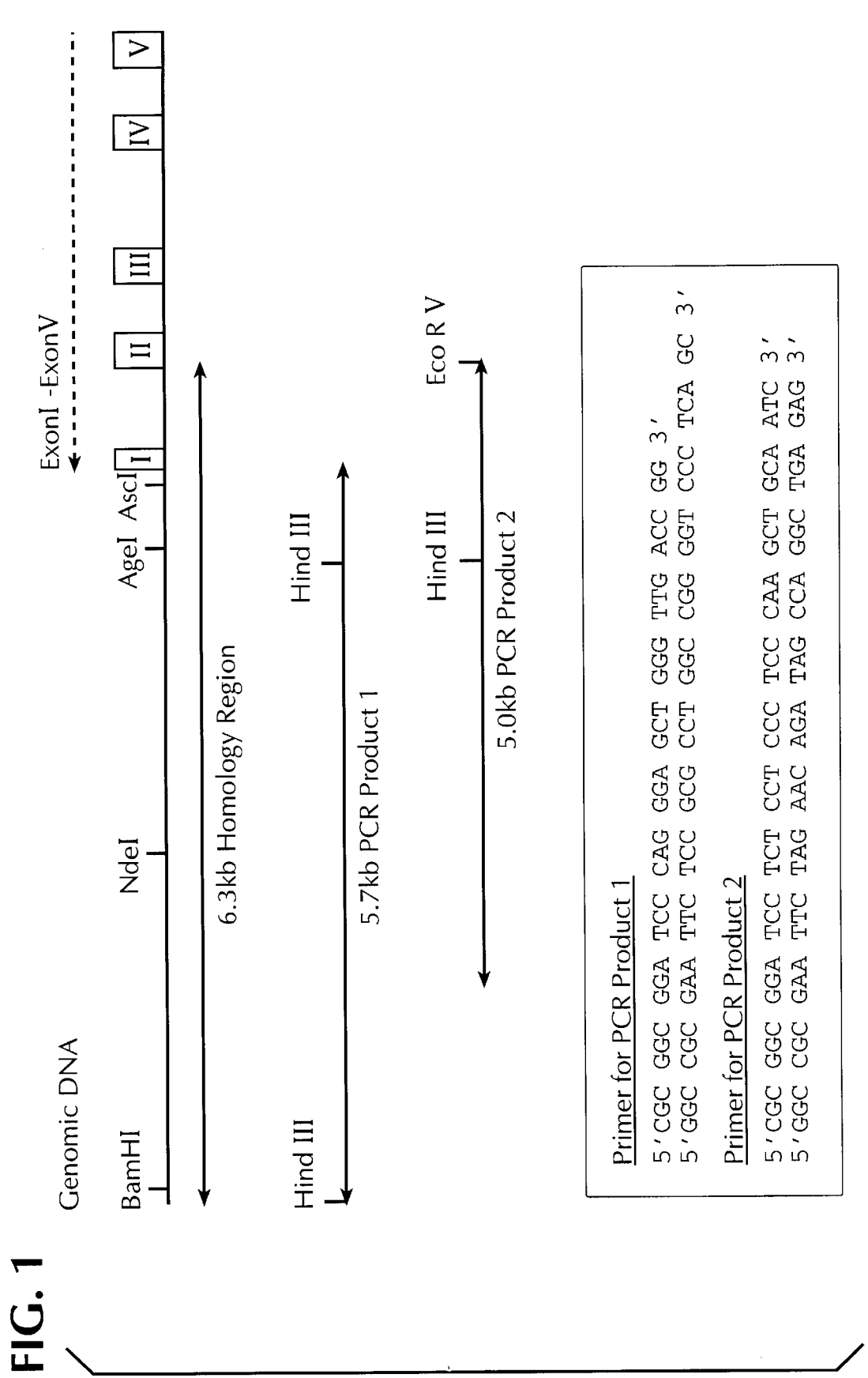

This application is a National Stage of application PCT/EP98/04590, filed Jul. 22, 1998, which claims the priority of U.S. application Ser. No. 09/113,692 filed Jul. 10, 1998.

The invention relates to human cells which are capable, on the basis of an activation of the endogenous human EPO gene, of producing EPO in sufficient amount and purity to permit economical preparation of human EPO as a pharmaceutical preparation. The invention furthermore relates to a method of preparing such human EPO-producing cells, DNA constructs for activating the endogenous EPO gene in human cells, and methods for the large-scale production of EPO in human cells.

Erythropoietin (EPO) is a human glycoprotein which stimulates the production of red blood cells. EPO occurs in the blood plasma of healthy persons only in very low concentrations, so that preparation in large amounts is not possible in this manner. EP-0148 605 and EP-B-0205 564 describe the preparation of recombinant human EPO in CHO cells. The EPO described in EP-B-0148 605 has a higher molecular weight than urinary EPO and no O-glycosylation. Meantime, the EPO described in EP-B-0 205 564 from CHO cells, is available in large amounts and in pure form, but it originates from nonhuman cells. Moreover, the ability of CHO cells to produce is often relatively limited.

Furthermore, the harvesting of human EPO from the urine of patients with aplastic anemia is known (Miyake et al., J. Biol. Chem. 252 (1977), 5558–5564). Therein a seven-step process is disclosed which includes ion exchanger chromatography, ethanol precipitation, gel filtration and adsorption chromatography. An EPO preparation with a specific activity of about 70,000 U/mg of proteins obtained in a 21% yield. Disadvantages of this process and other methods of obtaining urinary EPO consist in the procurement of starting material in sufficient amounts and in repeatable quality. Furthermore, the purification from urine is difficult and even a purified product is not free of urinary contaminants.

GB-A-2085 887 describes a method for the preparation of human lymphoblastoid cells which are capable of producing EPO in small amounts. The economical production of a pharmaceutical with these cells is not possible.

WO 91/06667 describes a method for the recombinant preparation of EPO. In a first process step in primary human embryo kidney cells the endogenous EPO gene is brought by homologous recombination into operable linkage with a viral promoter and the DNA is isolated from these cells. In a second step the DNA thus isolated is transformed into nonhuman CHO cells and the expression of EPO in these cells is analyzed. No mention is found that production of EPO in human cells is possible.

WO 93/09222 describes the production of EPO in human cells, wherein a relatively high EPO production of up to 960,620 mU/$10^6$ cells/24 h is found in human fibroblasts which had been transfected with a vector containing the complete EPO gene. These cells contain an exogenous EPO gene which is not at the correct EPO gene locus, so that problems are to be expected with regard to the stability of the cell line. No information on a constitutive EPO production is found in WO 93/092222. Furthermore, neither is there any information as to whether the EPO produced can be obtained in a quality sufficient for pharmaceutical purposes.

Furthermore, in WO 93/09222 an activation of the endogenous EPO gene in human HT1080 cells is described. In it an EPO production is found of only 2,500 mU/$10^6$ cells in 24 h (corresponding approximately to 16 ng/$10^6$ cells/24 h). Such low production is entirely unsuited for the economical production of a pharmaceutical preparation.

WO 94/12650 and WO 95/31560 describe how a human cell with an endogenous EPO gene activated by a viral promoter is able, after amplification of the endogenous EPO gene, to produce up to approximately 100,000 mU/$10^6$ cells/24 h (corresponding to about 0.6 µg/$10^6$ cells/24 h) of EPO. This amount too is still not sufficient for the economical production of a pharmaceutical.

The problem on which the present invention is based thus consisted in eliminating at least partially the above-described disadvantage of the state of the art and to offer a technologically better method for the preparation of EPO in human cells. Especially, this is to make it possible to obtain a product in sufficient quantity and purity to permit economical production for pharmaceutical purposes.

This problem is solved by activation of the endogenous EPO gene in human cells and if desired by subsequent amplification of the activated human EPO gene. In this manner it has surprisingly been possible, by the selection of suitable starting cells, DNA constructs and selection strategies, to provide human cells which are capable of producing EPO in sufficient quantity, quality and purity to permit the economical production of pharmaceutical preparations. Especially after amplification of the activated endogenous EPO gene, cells can be obtained which have a definitely higher production output than the CHO production cells used previously for the preparation of recombinant EPO.

One subject matter of the invention is a human cell which contains a copy of an endogenous EPO gene in operable linkage with a heterologous expression control sequence active in the human cell and is capable without prior gene amplification of producing at least 200 ng of EPO/$10^6$ cells per 24 hours. Preferably the human cell according to the invention is capable of the production of 200 to 3000 ng EPO/$10^6$ cells/24 h, and most preferably for the production of 1000 to 3000 ng EPO/$10^6$ cells/24 h.

Another subject matter of the present invention is a human cell which is obtainable by gene amplification from the cell previously described and contains several copies of an endogenous EPO gene, each in operable linkage with a heterologous expression control sequence active in the human cell, and is capable of the production of at least 1,000 ng EPO/$10^6$ cells/24 h. With special preference the human cell line obtainable by gene amplification is capable of producing 1,000 to 25,000 ng EPO/$10^6$ cells/24 h, and most preferably for the production of 5,000 to 25,000 ng EPO/$10^6$ cells/24 h.

The human cell is any cell, provided it can be cultured in vitro. Especially preferred are human cells which can be cultured in a serum-free medium, and especially in suspension.

In this manner the production of EPO can be performed in a large fermenter with a culture capacity of, for example, 1,000 liters.

Especially preferred is a human cell which is an immortalized cell, for example an HT 1080 cell (Rasheed et al., Cancer 33 (1974), 1027–1033), a HeLa S3 cell (Puck et al., J. Exp. Med. 103 (1956), 273–284), a Namalwa cell (Nadkarni et al., Cancer 23 (1969), 64–79) or a cell derived therefrom. An example of a cell according to the invention is the clone "Aladin" which was deposited on Jul. 15, 1997 according to the prescriptions of the Budapest Treaty at the Deutsche Sammlung von Mikroorganismen und Zellkulturen (DSMZ), Mascheroder Weg 1b, 38124 Braunschweig, under number DSM ACC 2320.

In the cell according to the invention, the endogenous EPO gene is linked with a heterologous expression control sequence which is active in the human cell. The expression control sequence comprises a promoter and preferably additional expression-improving sequences, e.g., an enhancer. The promoter can be a inducible or a constitutive promoter. Preferably the promoter is a strong viral promoter, e.g., an SV40 or a CMV promoter. The CMV promoter/enhancer is especially preferred.

Furthermore, to optimize the EPO expression it may be preferred for the endogenous EPO gene in the human cell, which is in operable association with the heterologous promoter, to have a signal peptide-coding sequence which is different from the natural signal peptide-coding sequence and codes preferably for a signal peptide with a modified amino acid sequence. Especially preferred is a signal peptide-coding sequence which codes for a signal peptide sequence modified in the region of the first four amino acids which is selected from $$\text{Met-}X_1\text{-}X_2\text{-}X_3,$$

wherein $X_1$ is Gly or Ser, $X_2$ is Ala, Val, Leu, Ile, Ser or Pro, and $X_3$ is Pro, Arg, Cys or His, on the condition that $X_1\text{-}X_2\text{-}X_3$ is not the sequence Gly-Val-His, and especially from (a) Met-Gly-Ala-His, (SEQ ID NO:8)
(b) Met-Ser-Ala-His SEQ ID NO:10
(c) Met-Gly-Val-Pro SEQ ID NO:12 or
(d) Met-Ser-Val-His SEQ ID NO:14.

It is especially preferred that the sequence of the first four amino acids of the signal peptide be Met-Ser-Ala-His SEQ ID NO:10.

In an additional aspect, the present invention relates to a method for preparing a human EPO-producing cell, as previously stated, comprising the steps:

(a) Preparing human starting cells which contain at least a copy of an endogenous EPO gene,
(b) Transfecting the cells with a DNA construct comprising:
  (i) two flanking DNA sequences which are homologous with regions of the human EPO gene locus, to permit a homologous recombination,
  (ii) a positive selection marker gene, and
  (iii) a heterologous expression control sequence which is active in the human cell,
(c) Culturing the transfected cells under conditions which select for the presence of the positive selection marker gene,
(d) Analyzing the cells selectable according to step (c), and
(e) Identifying the EPO-producing cells.

The DNA construct used in preparing the human EPO-producing cell contains two flanking DNA sequences which are homologous with regions of the human EPO gene locus in order to permit a homologous recombination. The selection of suitable flanking sequences is performed, for example, by the methods described in WO 90/11 354 and WO 91/09 955. Preferably the flanking sequences have each a length of at least 150 bp. With special preference the homologous DNA sequences are selected from the region of the 5'-untranslated sequences, exon 1 and intron 1 of the EPO gene. It is especially preferred to use a DNA sequence modified in the region of exon 1, which codes for a signal peptide modified in the first amino acids. The modifications in the exon 1 region are preferably as stated above.

The selection marker gene can be any selection marker gene suitable for eucaryotic cells, which upon expression leads to a selectable phenotype, e.g., antibiotic resistance, auxotrophy, etc. An especially preferred positive selection marker gene is the neomycin phosphotransferase gene.

Optionally, a negative selection marker gene such as, e.g., the HSV-thymidine kinase gene, can also be present, by whose expression cells are destroyed in the presence of a selection agent.

If an amplification of the EPO gene endogenously activated in the human cell is desired, the DNA construct contains an amplification gene. Examples of suitable amplification genes are dihydrofolate reductase, adenosine deaminase, ornithine decarboxylase, etc. An especially preferred amplification gene is the dihydrofolate reductase gene, especially a dihydrofolate reductase arginine mutant which has a lower sensitivity to the selective agent (methotrexate) than the wild type gene (Simonsen et al., Proc. Natl. Acad. Sci. USA 80 (1983); 2495).

If an amplification gene is present in the DNA construct used for activating the EPO gene, the method of the invention can also comprise the following steps:

(f) Amplification of the DNA sequence coding for EPO, and
(g) Harvesting of EPO-producing cells which contain a number of copies, greater in comparison with the starting cell, of an endogenous DNA sequence coding formature EPO in operable linkage with a heterologous expression control sequence.

Appropriate DNA constructs for the activation of the endogenous EPO gene present in the human starting cell are the plasmids listed in the examples: p187, p189, p190 and p192. Especially preferred is the plasmid p189 which was deposited with the DSMZ in accord with the provisions of the Budapest Treaty on Jul. 16, 1997 under the accession number DSM 11661, or a plasmid derived therefrom. The DNA constructs are preferably circular plasmid molecules which are used for the transfection of the human cell in a linearized form.

An additional subject of the present invention is a DNA construct for the activation of an endogenous EPO gene in a human cell, comprising:

(i) two flanking DNA sequences which are chosen homologous to regions of the human EPO gene locus selected from 5'-untranslated sequences, exon 1 and intron 1, in order to permit a homologous recombination, a modified sequence being present in the exon 1 region coding for the amino acids:

$$\text{Met-}X_1\text{-}X_2\text{-}X_3,$$

wherein $X_1$ is Gly or Ser, $X_2$ is Ala, Val, Leu, Ile, Ser or Pro, and $X_3$ is Pro, Arg, Cys or His, on the condition that $X_1\text{-}X_2\text{-}X_3$ is not the sequence Gly-Val-His, and especially for the amino acids:
(a) Met-Gly-Ala-His SEQ ID NO:8,
(b) Met-Ser-Ala-His SEQ ID NO:10,
(c) Met-Gly-Val-Pro SEQ ID NO:12 or
(d) Met-Ser-Val-His SEQ ID NO:14,
(ii) a positive selection marker gene, (iii) a heterologous expression control sequence which is active in a human cell, and (iv) in some cases an amplification gene.

Still another subject of the present invention is a DNA construct for the activation of an endogenous EPO gene in a human cell, comprising:

(i) two flanking DNA sequences which are homologous to regions of the human EPO gene locus, selected from 5'-untranslated sequences, exon 1 and intron 1, to permit a homologous recombination, (ii) a positive selection marker gene, (iii) a heterologous expression control sequence which is active in a human cell, the distance between the heterologous expression control sequence and the translation start of the EPO gene being no greater than 1100 bp, and (iv) in some cases, an amplification gene.

Surprisingly it was found that, in the case of a modification of the EPO signal sequence and/or a shortening of the distance between the heterologous expression control sequence and the translation start of the EPO gene, an optimized expression is obtained. Preferably the distance between the promoter of the heterologous expression control sequence and the translation start of the EPO gene is not greater than 1100 bp, especially preferred is not more than 150 bp, and most preferably not more than 100 bp. An especially preferred example of a DNA construct to be used according to the invention is the plasmid p189 (DSM 11661) or a plasmid derived therefrom.

Still another aspect of the present invention is a method for preparing human EPO, wherein a human cell according to the invention is cultured in a suitable medium under conditions in which a production of EPO takes place and the EPO is harvested from the culture medium. A serum-free medium is used preferentially. The cells are preferably cultured in suspension. More preferred, the culturing is performed in a fermenter, especially in a large fermenter with a capacity of, for example, 10 l–50,000 l.

The harvesting of human EPO from the culture medium of human cell lines comprises preferably the following steps:

(a) Passing the cell supernatant over an affinity chromatography medium and harvesting the fractions containing EPO, (b) optionally, passing the EPO-containing fractions over a hydrophobic interaction chromatography medium and harvesting the EPO-containing fractions, (c) passing the EPO-containing fractions over hydroxyapatite and harvesting the EPO-containing fractions, and (d) concentrating and/or passing over a reverse-phase (RP) HPLC medium.

Step (a) of the purification process includes passing the cell supernatant, which in some cases can be pre-treated, over an affinity chromatography medium. Preferred affinity chromatography media are those to which a blue dye is coupled. An especially preferred example is blue sepharose.

After elution from the affinity chromatography medium the EPO-containing eluate is passed, in some cases, over a hydrophobic interaction chromatography medium. This step is expedient if a culture medium with a serum content≧2% (v/v) is used. If a culture medium with a low serum content is used, e.g., 1% (v/v), or a serum-free medium is used, this step can be omitted. A preferred hydrophobic interaction chromatography medium is butyl-sepharose.

The eluate from step (a) or, if used, step (b), is passed in step (c) of the method of the invention over hydroxyapatite and the EPO-containing eluate is subjected to a concentrating step and/or a reverse-phase HPLC purification step. The concentration is performed preferably by exclusion chromatography, e.g., membrane filtration, the use of a medium, such as a membrane with an exclusion size of 10 kD, having proven desirable.

By the method according to the invention an isolated human EPO with a specific activity of at least 100,000 U/mg protein in vivo (normocythemic mouse) is obtainable, which is free from urinary contaminants and can differ in its glycosylation from recombinant EPO from CHO cells. Preferably, the EPO of the invention has a specific activity of at least 175,000, and with special preference at least 200,000 to 400,000 or 450,000 IU/mg protein. The human EPO obtainable by the method of the invention can contain α-2,3- and/or α-2,6-linked sialic acid residues. In studies of EPO from cells which contain an endogenously activated EPO gene, on the basis of the present preliminary results, the presence of α-2,3- and α-2, 6-linked sialic acid residues were found. Furthermore, it was found on the basis of the present preliminary results that the human EPO of the invention has a content of less than 0.2% N-glycol neuraminic acid, with respect to the content of N-acetyl neuraminic acid.

The purity of the human EPO of the invention amounts preferably to at least 90%, more preferably at least 95%, and most preferably at least 98% of the total protein content. The determination of the total protein content can be performed by reverse phase HPLC, e.g., with a Poros R/2H column.

Furthermore, by the method of the invention, human EPO species are obtain able which differ in their amino acid sequence. Thus it was found by mass spectrometric analysis (MALDI-MS) that a human EPO can be isolated from HeLa S3 cells, which is mainly a polypeptide with a length of 165 amino acids, which is formed by C-terminal processing of an arginine residue, and in some cases includes up to 15% of an EPO with 166 amino acids. Also, a human EPO is obtainable which includes a polypeptide with a length of 166 amino acids, i.e., a non-processed EPO. From Namalwa cells, for example, a human EPO has been isolated which comprises a mixture of polypeptides with a length of 165 and 166 amino acids.

This human EPO can be used as an active substance for a pharmaceutical preparation which can contain additional active substances, as well as pharmaceutically common adjuvants, vehicles and additives.

In still another aspect the present invention relates to an isolated DNA which codes for a human EPO with a sequence modified in the region of the first four amino acids of the signal peptide, which is selected from:

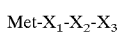

wherein $X_1$ is Gly or Ser, $X_2$ is Ala, Val, Leu, Ile, Ser or Pro, and $X_3$ is Pro, Arg, Cys or His, on the condition that $X_1$-$X_2$-$X_3$ is not the sequence Gly-Val-His, and especially for the amino acids:

(a) Met-Gly-Ala-His SEQ ID NO:8, (b) Met-Ser-Ala-His SEQ ID NO:10

(c) Met-Gly-Val-Pro SEQ ID NO:12 or (d) Met-Ser-Val-His SEQ ID NO:14.

The DNA can be for example a genomic DNA or a cDNA.

The invention will continue to be exemplified by the following examples and illustrations and sequence listings. The drawings are as follows:

FIG. 1 A schematic representation of the amplification of homology regions of the EPO gene from the region of the 5'-untranslated sequences, exon 1 and intron 1.

Figure 2:
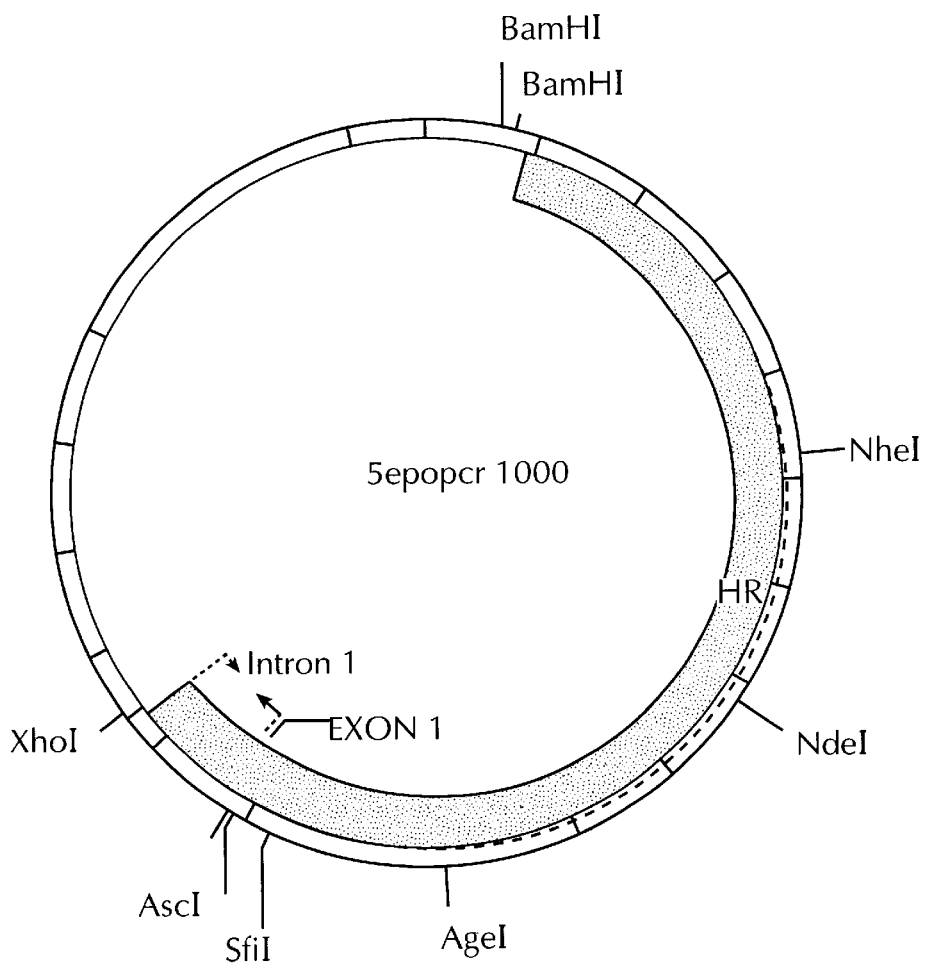

FIG. 2 A schematic representation of a plasmid which contains EPO homology regions from the region of the 5'-untranslated sequences, exon 1 and intron 1.

Figure 3:

FIG. 3 A schematic representation of a gene-activation sequence which contains the Rous sarcoma virus promoter (RSV), the neomycin phosphotransferase gene (NEO), the early polyadenylation region of SV40 (SVI pA), the early SV40 promoter (SVI), the dihydrofolate reductase gene (DHFR), an additional early SV40 polyadenylation region, and the cytomegalovirus immediate early promoter and enhancer (MCMV).

Figure 4A:
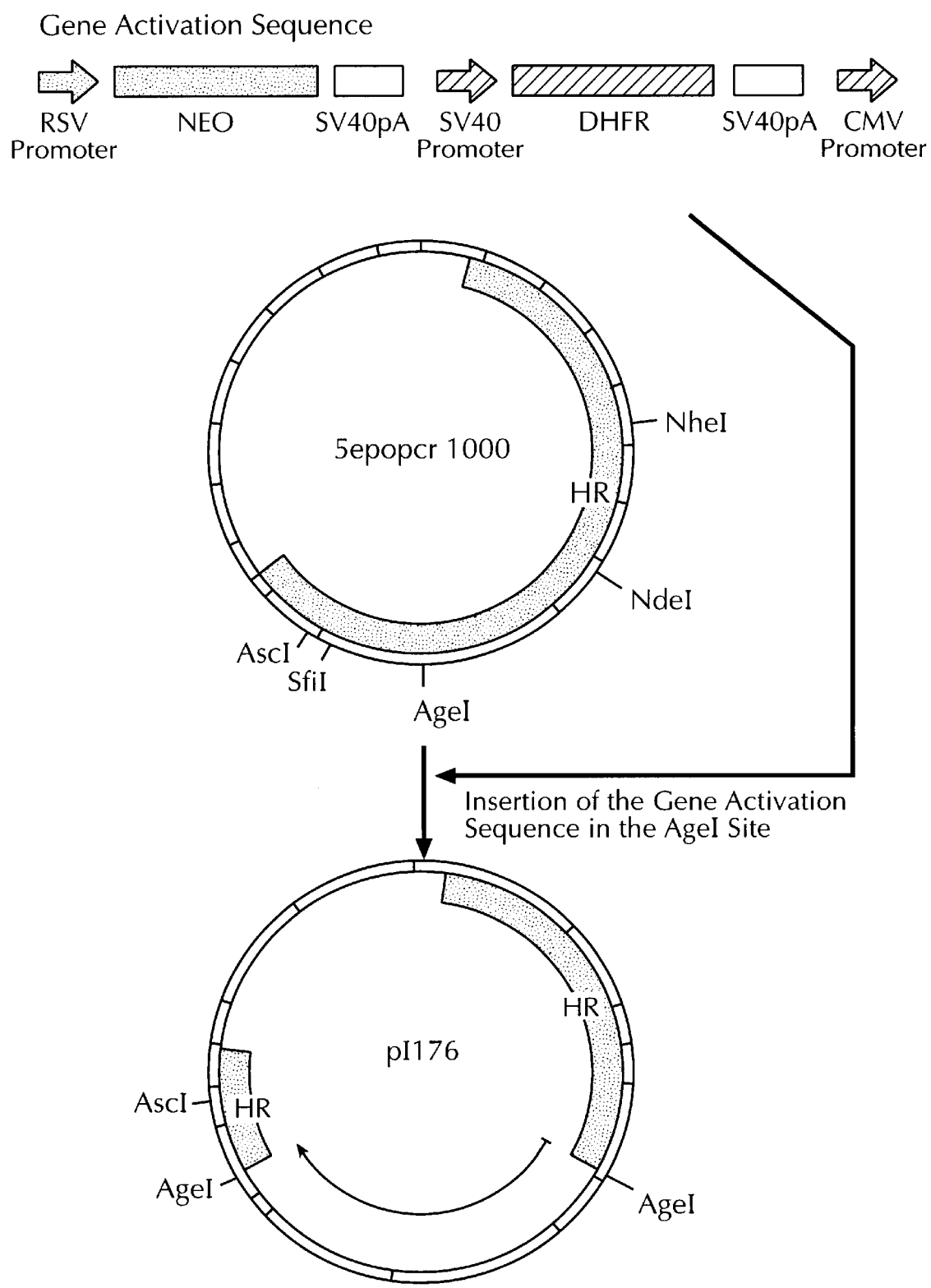

FIG. 4a The preparation of the EPO gene targeting vector p176.

Figure 4B:
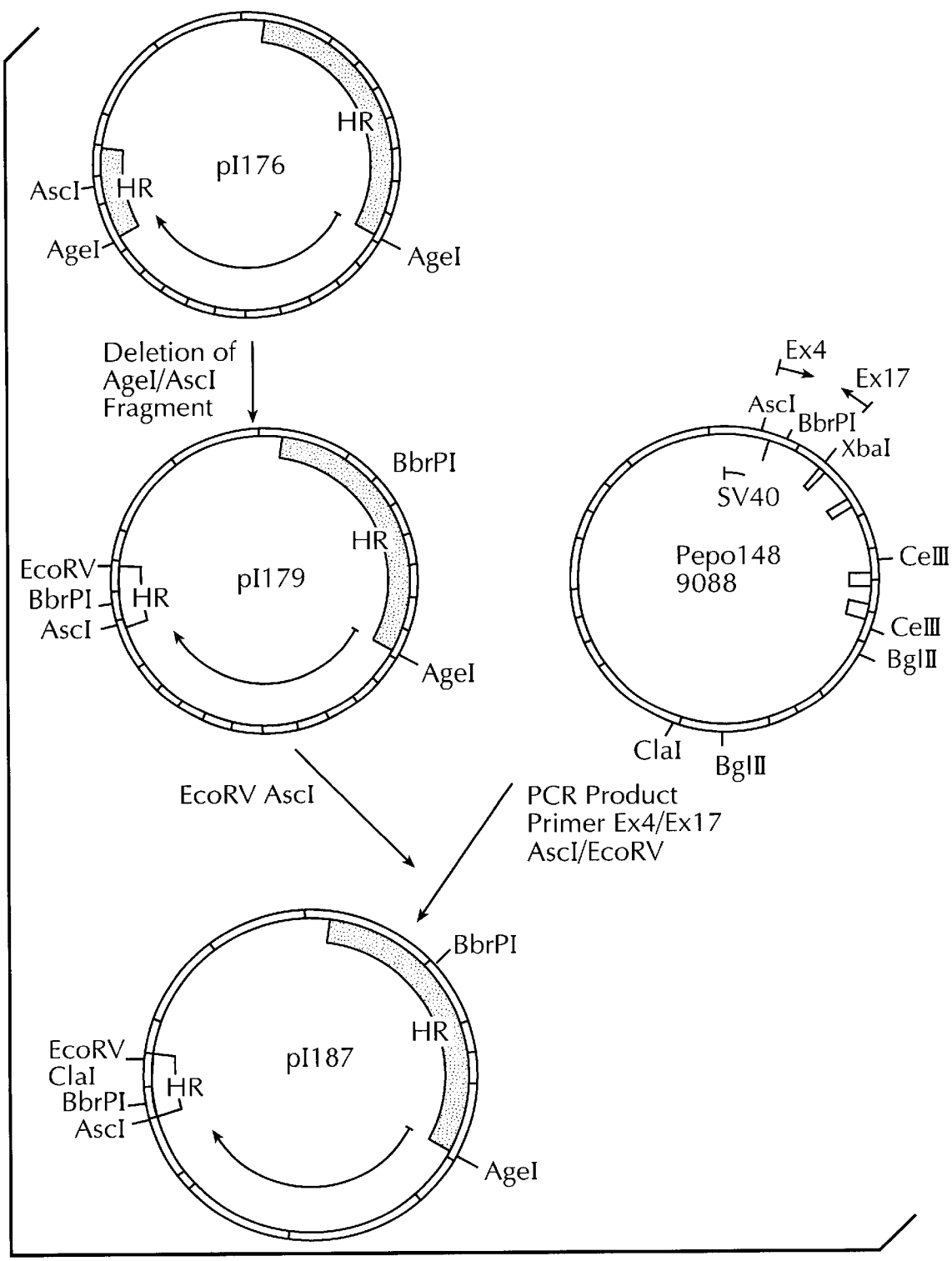

FIG. 4b The preparation of the EPO gene targeting vectors p179 and p187.

Figure 4C:
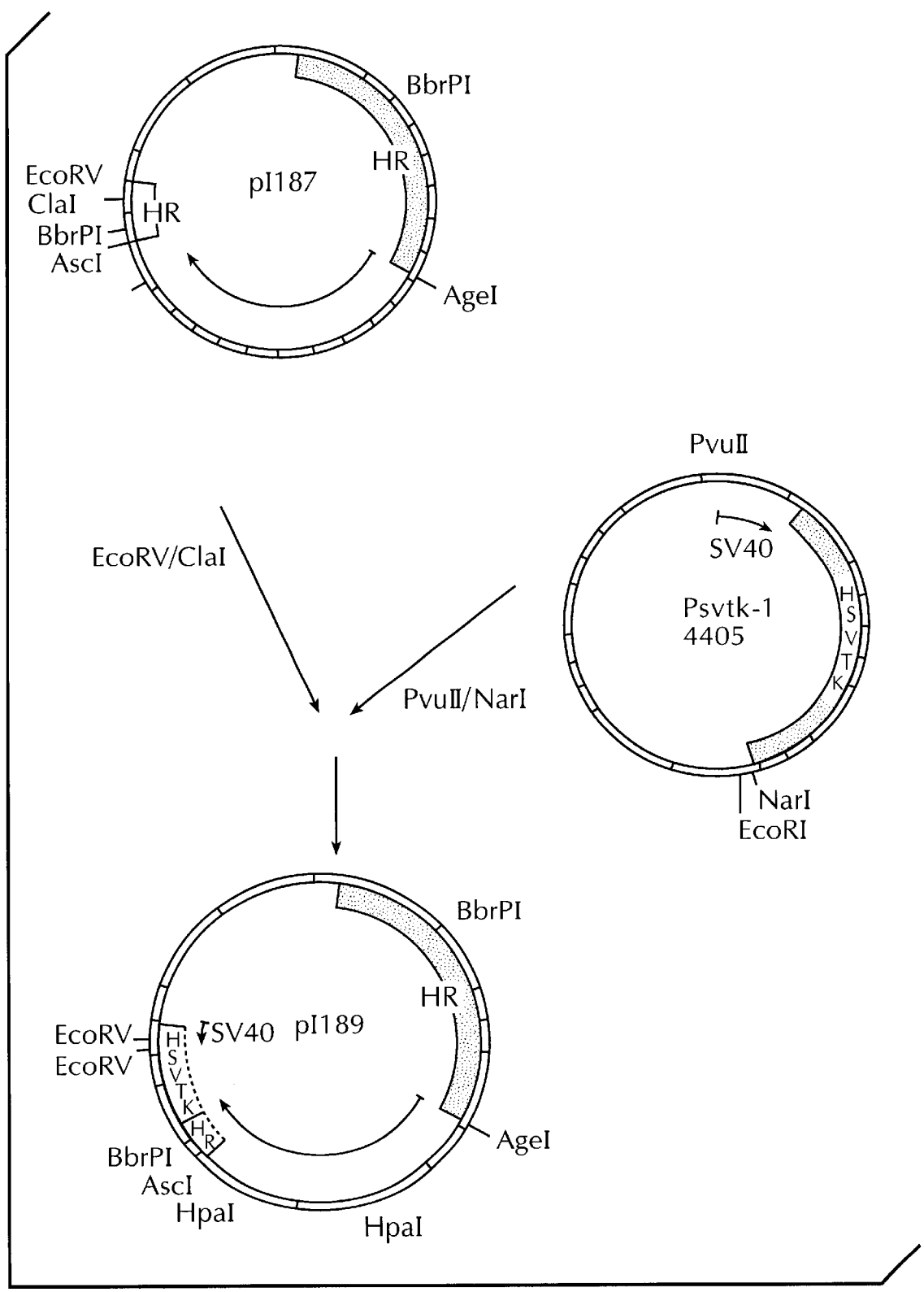

FIG. 4c The preparation of the EPO gene targeting vector p189 (DSM 11661).

Figure 4D:
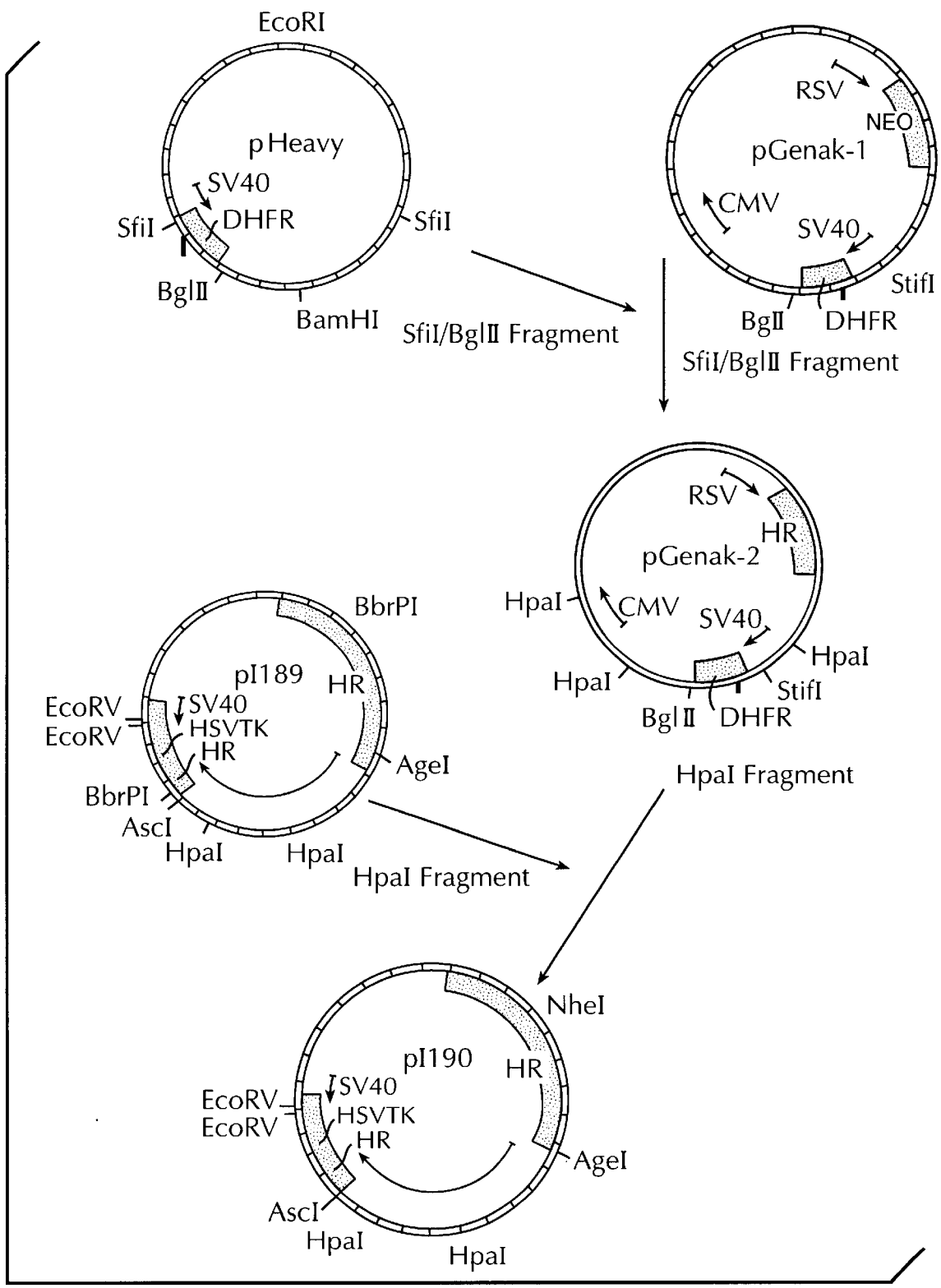

FIG. 4d The preparation of the EPO gene targeting vector p190.

Figure 4E:
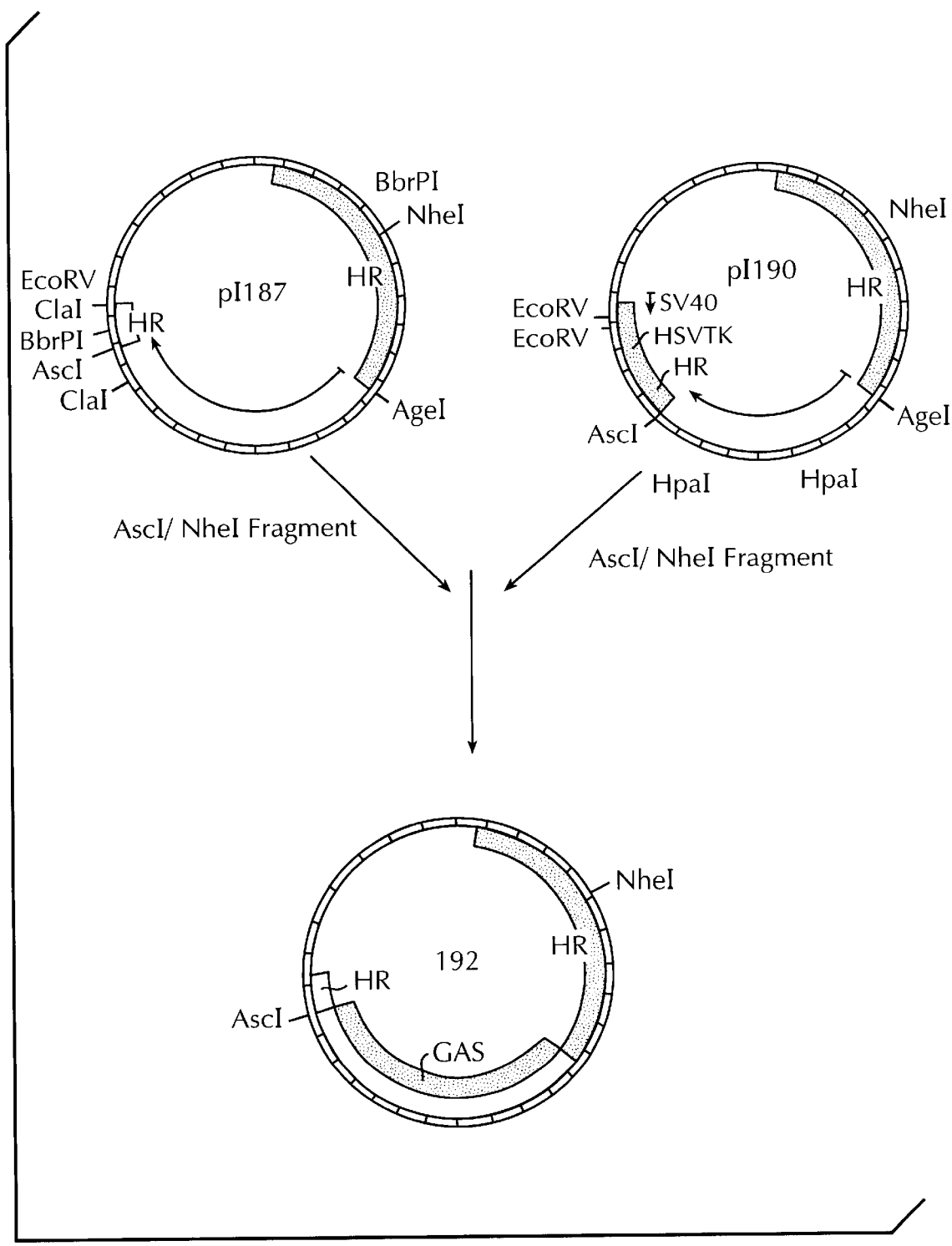

FIG. 4e The preparation of the EPO gene targeting vector p192.

Figure 5:
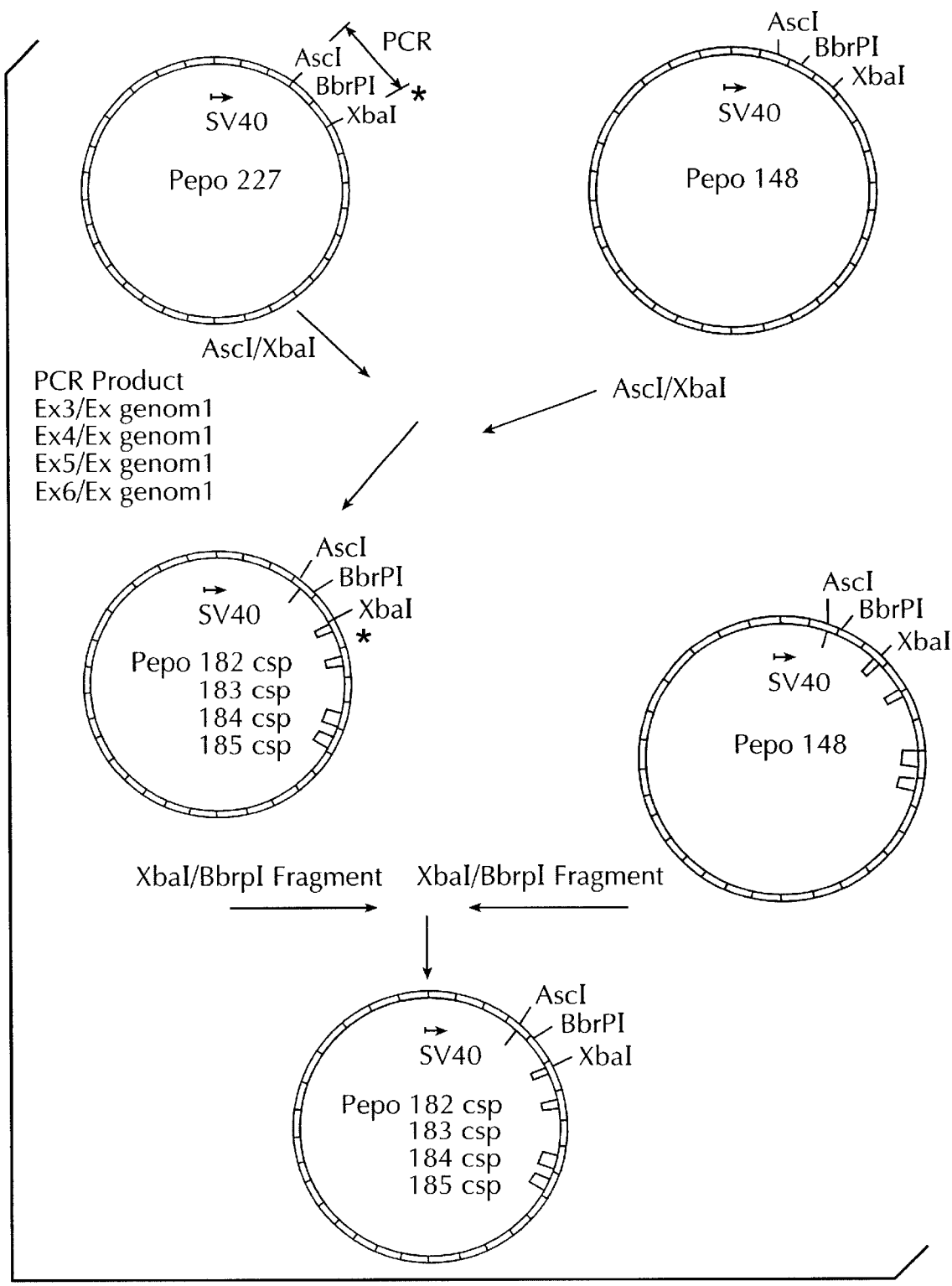

FIG. 5 A schematic representation of the preparation of EPO cDNA with signal sequence mutations.

Figure 6A:
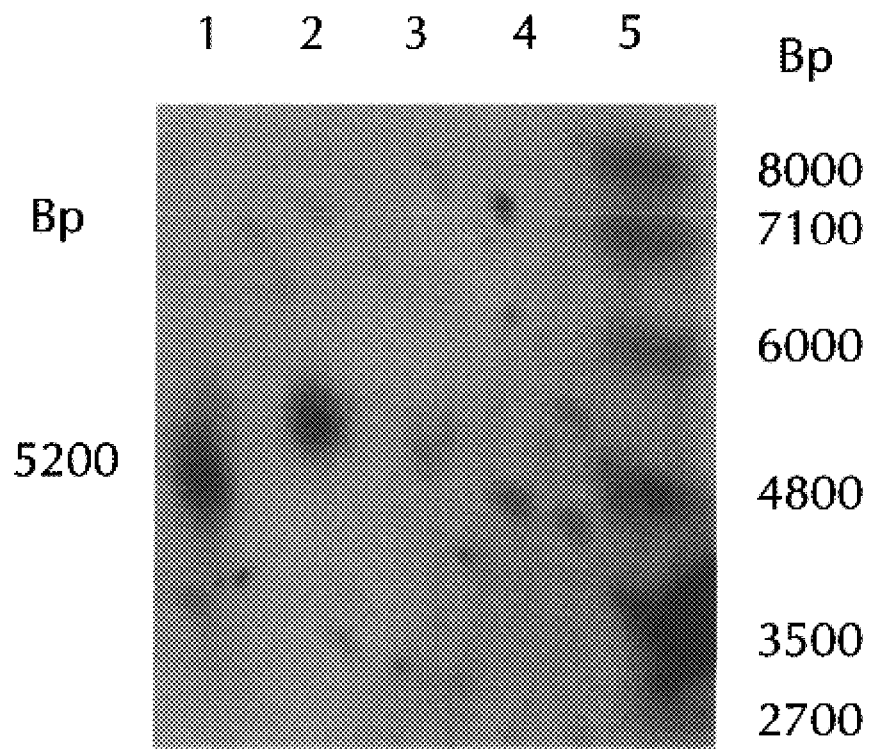

FIG. 6a The hybridization of cellular DNA with a probe from the CMV region of the gene cassette represented in FIG. 3; the lanes 1 to 4 are each of DNA from human cells cleaved with the restriction enzymes AgeI and AscI; lane 1: EPO-producing HeLa S3 cell amplified with 1,000 nM MTX; lane 2: EPO-producing HeLa S3 cell amplified with 500 nM MTX; lane 3: EPO-producing HeLa S3 Cell without amplification; lane 4: HeLa S3 cell without activated EPO gene; lane 5: digoxigenin labeled size marker; the size of the hybridizing fragment in lanes 1 to 3 is approximately 5,200 bp, and FIG. 6b The hybridization of a probe from the coding region of EPO with DNA from human cells; lane 1: digoxigenin-labeled size marker; lanes 2 to 4: DNA from human cells cleaved with the restriction enzymes BamHI, HindIII and SalI; lane 2: EPO producing HeLa S3 cell amplified with 500 nM MIX (length of the band produced by the non-activated endogenous gene: 3,200 bp; length of the copy of the EPO gene activated by gene targeting: 2,600 bp); lane 3: DNA from an EPO producing HeLa S3 cell not amplified; lane 4: DNA from an HeLa S3 control cell.

SEQ ID No. 1 and No.2 Nucleotide sequences of the primers used for preparing PCR Product 1 (FIG. 1).

SEQ ID No. 3 and No. 4 Sequences of the primers used for preparing PCR Product 2 (FIG. 1).

SEQ ID No. 5 Sequence of the primer EPO EX1.

SEQ ID No. 6 Sequence of the primer EX2.

SEQ ID No. 7 Sequence of the primer EX3 (Met-Gly-Ala-His).

SEQ ID No. 8 Sequence of the modified signal peptide start coded by primer EX3.

SEQ ID No. 9 Sequence of primer EX4 (Met-Ser-Ala-His).

SEQ ID No. 10 Sequence of the modified signal peptide start coded by primer EX4.

SEQ ID No. 11 Sequence of primer EX5 (Met-Gly-Val-Pro).

SEQ ID No. 12 Sequence of the modified signal peptide start coded by primer EX5.

SEQ ID No. 13 Sequence of primer EX6 (Met-Ser-Val-His).

SEQ ID No. 14 Sequence of the modified signal peptide start coded by primer EX6.

SEQ ID No. 15 Sequence of primer EX genome 1.

SEQ ID No. 16 Sequence of primer EX13.

SEQ ID No. 17 Sequence of primer EPO EX 17.

EXAMPLES

The activation of the EPO gene locus for protein production on an industrial scale was achieved by homologous integration of a gene activation sequence which contains the neomycin phosphotransferase (NEO) gene for the selection (G-418 resistance), the murine dihydrofolate reductase (DHFR) gene (for gene amplification by MTX) and the cytomegalovirus (CMV) immediate early promoter and enhancer for gene activation.

Example 1

Cloning of EPO Homology Regions

Homology regions of the EPO gene were amplified by using a genomic placenta DNA (Boehringer Mannheim). Two PCR products were prepared from a homology region 6.3 kB long from the region of the 5'-untranslated sequences of the EPO gene, exon 1 and intron 1 (cf. FIG. 1). The primers used for the preparation of PCR Product 1 had the following sequences: 5'-CGC GGC GGA TCC CAG GGA GCT GGG TTG ACC GG-3' (SEQ ID No. 1) and 5'-GGC CGC GAA TTC TCC GCG CCT GGC CGG GGT CCC TCA GC-3' (SEQ ID No. 2). The primers used for the preparation of PCR Product 2 had the following sequences: 5'-CGC GGC GGA TCC TCT CCT CCC TCC CAA GCT GCA ATC-3' (SEQ ID No. 3) and 5'-GGC CGC GAA TTC TAG AAC AGA TAG CCA GGC TGA GAG-3' (SEQ ID No. 4).

The desired segments were cut out of PCR Products 1 and 2 by restriction cleavage (PCR Product 1: HindIII, PCR Product 2: HindIII and Eco RV) and cloned into the vector pCRII (Invitrogen) which had been cleaved with Hind III and Eco RV. The recombinant vector obtained in this manner was named 5 epopcr 1000 (cf. FIG. 2).

Example 2

Construction of EPO Gene Targeting Vectors 2.1 A gene activation sequence which contains the NEO gene, the DHFR gene and a CMV promoter/enhancer (cf. FIG. 3) was inserted into the AgeI site of the plasmid 5epocr1000 containing the EPO homology region, and the plasmid p176 was obtained (cf. FIG. 4a). To bring the CMV promoter as close as possible to the translation start site of the EPO gene, a segment 963 bp long was deleted between the restriction sites AscI and AgeI (partial cleavage), whereupon the plasmid p179 was obtained (FIG. 4b).

2.2 To optimize the expression, nucleotides in exon 1, which code for the beginning of the EPO leader sequence Met-Gly-Val-His, were replaced by the synthetic sequence Met-Ser-Ala-His (cf. also Example 6). This sequence was obtained by amplification of a genomic EPO-DNA sequence, e.g., of the plasmid pEP0148, which contains a 3,5 kB BstEII/EcoRI fragment (including the exons 1–5) of the human EPO gene sequence under the control of the SV40 promoter (Jacobs et al., Nature 313 (1985), 806 and Lee-Huang et al., Gene 128 (1993), 227) as template with the primers Ex4 (SEQ ID No. 9) and Ex17 (SEQ ID No. 17) (Table 1). The plasmid p187 was thus obtained (FIG. 4b).

2.3 The plasmid p189 was prepared from the plasmid p187 by insertion of the herpes simplex virus thymidine kinase gene (HSV-TK) which originated from Psvtk-1 (PvuII/ NarI fragment) (FIG. 4c). The HSV-TK gene is under control of the SV40 promoter at the 3' end of intron 1 (Eco RV/ClaI) in an opposite orientation relative to the CMV promoter and should serve for negative selection for a homologous recombination.

2.4 For the construction of plasmid p190, an SfiI/BglII fragment of pHEAVY, a plasmid which contains the cDNA of an arginine mutant of DHFR described in Simonsen et al. (Proc. Natl. Acad. Sci, USA 80 (1983), 2495) was subcloned into the plasmid pGenak-1 cut with SfiI and BglII, which contains the NEO gene under control of the RSV promoter and the late SV40 polyadenylation site as terminator, the murine DHFR gene under control of the early SV40 promoter and of the early SV40 polyadenylation site as terminator (Kaufmann et al., Mol. Cell. Biol.2 (1982), 1304; Okayama et al., Mol. Cell. Biol. 3 (1983), 280, and Schimke, J. Biol. Chem. 263 (1988), 5989) and the CMV promoter (Boshart et al., Cell 41 (1995) 521). Then an HpaI fragment which contained the cDNA coding for the DHFR arginine mutant was ligated into the plasmid p189 cut with HpaI, whereupon the plasmid p190 was obtained (FIG. 4d).

2.5 To obtain a transfection vector without the HSV-TK gene, an AscI/NheI fragment of the plasmid p190, which contained the gene activation sequence, was ligated into an AscI/NheI fragment, containing the exon 1, of the plasmid p187. The resulting plasmid was named p192 (FIG. 4e).

Example 3

Transfection of Cells

Various cell lines were selected for the production of EPO and transfected with targeting vectors.

3.1 Namalwa Cells

The cells were cultured in T150 tissue culture bottles and transfected by electroporation ($1 \times 10^7$ cells/800 μl of electroporation buffer 20 mM Hepes, 138 mM NaCl, 5 mM KCl, 0.7 mM $Na_2HPO_4$, 6 mM D-glucose monohydrate pH 7.0, 10 μg linearized DNA, 960 JIF, 260 V BioRad Gene Pulser). After the electroporation the cells were cultured in RPMI 1640, 10% (v/v) of fetal calf serum (FCS), 2 mM of L-glutamine, 1 mM of sodium pyruvate in forty 96-well plates. After two days the cells were cultured for 10 to 20 days in medium containing 1 mg/ml G-418. The supernatant was assayed in a solid-phase ELISA for the production of EPO (see Example 4). The EPO producing clones were expanded in 24-well plates and T-25 tissue culture bottles. Aliquots were frozen and the cells were subcloned by FACS (Ventage, Becton Dickinson). The subclones were repeatedly assayed for EPO production.

3.2 HT 1080 Cells

The conditions were as described for Namalwa cells, except that the HT1080 cells were cultivated in DMEM, 10% (v/v) FCS, 2 mM of L-glutamine, 1 mM of sodium pyruvate. For transfection by electroporation the cells were released from the walls of the culture vessels by trypsinization. After electroporation $1 \times 10^7$ cells were cultured in DMEM, 10% (v/v) FCS, 2 mM L-glutamine, 1 mM sodium pyruvate in five 96-well plates.

3.3 HeLa S3 Cells

The conditions were as described for Namalwa cells, except that the HeLa cells were cultured in RPM 1640, 10% (v/v) FCS, 2 mM L-glutamine, 1% (v/v) MEM nonessential amino acids (Sigma), and 1 mM sodium pyruvate. For transfection by electroporation the cells were released from the walls of the culture vessels by trypsinization. The conditions for the electroporation were 960 μF/250 V. After the electroporation the cells were cultured in RPMI 1640, 10% (v/v) FCS, 2 mM L-glutamine, 1% (v/v) MEM, 1 mM sodium pyruvate in T75 tissue culture bottles. 24 hours after electroporation the cells were trypsinized and cultured for 10 to 15 days in a medium containing 600 μg/ml of G-418 in ten 96-well plates.

Example 4

Selection for EPO-Producing Clones

The culture supernatant of transfected cells was assayed in an EPO ELISA. All steps were performed at room temperature. 96-well plates previously coated with streptavidin were coated with biotinylated anti-EPO antibodies (Boehringer Mannheim). For coating, the plates were first washed with 50 mM of sodium phosphate pH 7.2, and 0.05% (v/v) Tween 20. Then 0.01 ml of coating buffer (4 μg/ml of biotinylated antibody, 10 mM sodium phosphate pH 7.2, 3 g/l bovine serum albumin, 20 g/l sucrose, and 9 g/l NaCl) were added per well, and incubated at room temperature for 3 h. Then the plates were washed with 50 mM of sodium phosphate pH 7.2, dried and sealed.

Before the test, after washing the plates three times with 0.3 ml of phosphate-buffered saline (PBS) and 0.05% Tween 20 (Sigma), the plates were incubated overnight with 0.2 ml PBS 1% (w/v) crotein (Boehringer Mannheim) per well in order to block non-specific binding.

After removal of the blocking solution, 0.1 ml of culture supernatant was added and the plates were incubated overnight. The individual wells were washed three times with 0.3 ml of PBS and 0.05% Tween 20 each time. Then 100 μl of peroxidase (POD) conjugated monoclonal antibody (Boehringer Mannheim, 150 mU/ml) was added for two hours. The wells were then again washed three times with 0.3 ml of PBS and 0.05% Tween 20 each time. Then the peroxidase reaction was performed using ABTS® as substrate in a Perkin Elmer Photometer at 405 nm. A standard calibration curve using recombinant EPO from CHO cells (Boehringer Mannheim, 100–1000 pg/well) was used to calculate the EPO concentrations.

Example 5

EPO Gene Amplification

To increase the EPO expression the EPO-producing clones were cultured in the presence of increasing concentrations (100 pM–1000 nM) of methotrexate (MTX). The clones were assayed at each MTX concentration by an ELISA (see Example 4) for the production of EPO. Strong producers were subcloned by limiting dilution.

Example 6

Signal Sequence Mutations

To optimize the leader sequence of the EPO molecule, the first amino acids coded by exon 1 were replaced. Primers with different sequences (SEQ ID No. 4–17, the 3' primer contained a CelII site for the selection of modified sequences) were used in order to obtain as template an AscI/XbaI fragment by PCR using plasmid pEPO227 which contains a 4 kb HindIII/EcoRI fragment (including exons 1–5) of the human EPO gene sequence under control of the SV40 promoter (Jacobs et al., Nature 313 (1985), 806; Lee-Huang et al., Gene 128 (1993), 227). The resulting fragments were then cloned into the plasmid pEPO148 (Example 2.2), and the plasmids pEPO 182, 183, 184 and 185 were obtained (FIG. 5). The EPO gene expression was driven by an SV40 promoter. COS-7 cells were transfected transiently with the constructs (DEAE dextran method) and the cells were assayed 48 h after transfection for EPO production.

The mutated leader sequence Met-Ser-Ala-His obtained in this manner with the best EPO expression was used for constructing the gene targeting vectors (cf. Example 2.2).

Example 7

Characterization of EPO-Producing Cell Lines

Three different cell lines (Namalwa, HeLa S3 and HT 1080) were selected for the EPO gene activation. EPO-producing clones were obtained by transfection with the plasmids p179, p187, p189, p-190 or p192 (cf. Examples 2 and 3).

Approximately 160,000 NEO-resistant clones were assayed for EPO production, of which 12 to 15 secreted EPO reproducibly in significant yield into the cell supernatant.

Of these a total of 7 EPO clones were identified surprisingly without gene amplification by MTX which produced EPO in sufficient amounts for a large industrial production. The EPO production of these clones ranged from 200 ng/ml to more than 1000 ng/ml/$10^6$ cells/24 h. An example of one such cell is the clone "Aladin" deposited with the DSMZ (DSM ACC 2320), which was obtained from a Namalwa cell.

After gene amplification with 500 nM of MTX the EPO production of the identified EPO clones was increased to more than 3000 ng/ml/$10^6$ cells/24 h. An additional increase of the MTX concentration to 1000 nM led to a production of up to more than 7000 ng/ml/$10^6$ cells/24 h.

The clones obtained also showed EPO production under serum-free culture conditions.

Example 8

Characterization of the Genome of EPO-Producing Clones 8.1 Methodology

Human genomic DNA was isolated from about 108 cells and quantified (Sambrook et al., 1989). After cleavage of the genomic DNA with restriction enzymes, e.g., AgeI and AscI, and BamHI, HindIII and SalI, respectively, the DNA fragments were separated by their size by agarose gel electrophoresis and finally transferred to a nylon membrane and immobilized.

The immobilized DNA was hybridized with digoxigenin-labeled EPO probes or gene activation sequence-specific DNA probes (DIG DNA Labeling Kit, Boehringer Mannheim) and washed under stringent conditions. The specific hybridization signals were detected by means of a chemiluminescence method using radiation-sensitive films.

8.2 Results

The treatment of cells with 500 nM of MTX led to an increase of the hybridization signal at the EPO locus by a factor of 5 to 10. Upon an additional increase to 1000 nM MTX an increase by a factor>10 was obtained (FIG. 6a).

Figure 6B:
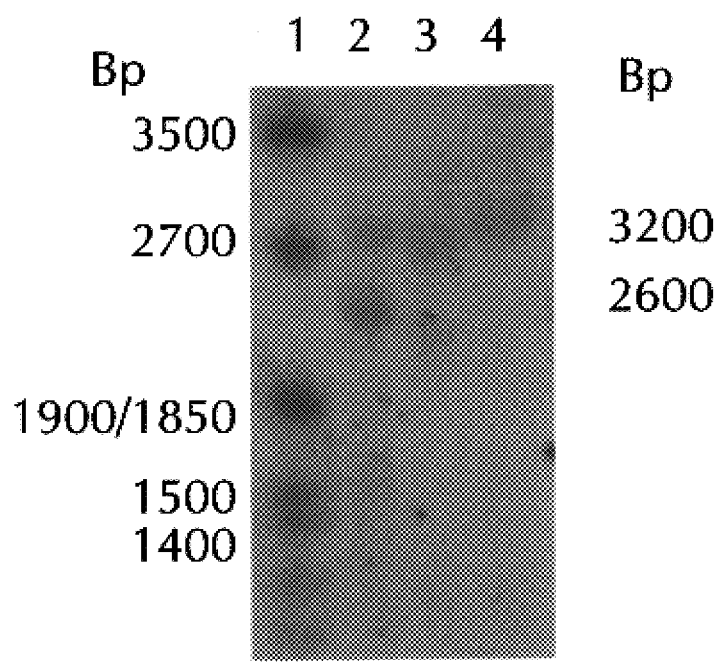

In the case of hybridization with the EPO specific probe, the copies of chromosome 7 that were unaffected by homologous recombination were also detected. As can be seen in FIG. 6b, these likewise hybridizing DNA fragments have a different, clearly distinguishable size and are not changed in their signal strength by the use of MTX.

Example 9

Purification of EPO from Culture Supernatants of Human Cell Lines (HeLa S3; Namalwa and HT1080)

For the purification of EPO from cell culture Supernatants of human cell lines, basically two methods were used, which differ in number and principle of the chromatography steps and were used depending on the composition of the medium and the EPO concentration:

| Method 1: | 1st step: | blue sepharose column |
| --- | --- | --- |
| | 2nd step: | butyl-sepharose column |
| | 3rd step: | hydroxyapatite column |
| | 4th step: | concentration |
| Method 2: | 1st step: | blue sepharose column |
| | 2nd step: | hydroxyapatite column |
| | 3rd step: | concentration |
| | (alternative 3rd step: RP-HPLC) | |

Example of purification of an HeLaS3 cell culture supernatant with 2% (v/v) fetal calf serum (FCS) by method 1:

1. Blue Sepharose Column

A 5 ml Hi-Trap-Blue column (Pharmacia's blue sepharose ready to-use column) was balanced with at least 5 column volumes (CV) of buffer A (20 mM Tris-HCl, pH 7.0; 5 mM $CaCl_2$; 100 mM NaCl). Then 70 ml of HeLa cell supernatant (containing approx. 245 µg EPO and 70–100 mg total protein) was drawn up overnight at a flow of 0.5 ml/min by the circulatory method, The column was washed with at least 5 CV of buffer B (20 mM Tris-HCl, pH 7.0, 5 mM $CaCl_2$; 250 mM NaCl) and with at least 5 CV buffer C (2mM Tris-HCl, pH 7.0; 0.2 MM $CaCl_2$, 250 mM NaCl) at 0.5 ml/min. The success of the washing was followed by measuring the protein content at OD280.

The elution of EPO was performed with buffer D (100 mM Tris-HCl, pH 7.0; 0.2 mM $CaCl_2$; 2 M NaCl) at a flow of 0. 5 ml/min. The elution solution was collected in 1–2 ml fractions.

The EPO content of the fractions, wash solutions and the flow was determined by reverse phase (RP)-HPLC by applying an aliquot to a POROS R2/H column (Boehringer Mannheim). Alternatively, an immunological dot blot was performed for the qualitative identification of fractions containing EPO.

Fractions containing EPO (8–12 ml) were pooled and applied to a butyl-sepharose column.

The yield after the blue sepharose column was about 175 µg EPO (corresponds to about 70%). In general the yield after blue sepharose was between 50 and 75%.

2. Butyl Sepharose Column (Hydrophobic Interaction Chromatography

A self-made 2–3 ml butyl sepharose column (material: Toyopearl Butyl S650) was balanced with at least 5 CV of buffer D (100 mM Tris HCl, pH 7.0; 0.2 mM $CaCl_2$ and 2 M NaCl) and then the blue sepharose pool containing EPO was drawn up from 1. (approx. 150 µg EPO) at a flow of 0.5 ml/min.

The column was washed at 0.5 ml/min with at least 5 CV of buffer E (20 mM Tris-HCl, pH 7.0; 2 M NaCl and 10% isopropanol). The washing effect was monitored by measuring the protein content at OD280.

The elution of EPO was performed with buffer F (20 mM Tris-HCl, pH 7.0; 2 M NaCl and 20% isopropanol) at a flow of 0.5 ml/min. The elution solution was collected in 1–2 ml fractions.

The EPO content of the fractions, the wash solutions and the flow was determined by RP-HPLC by applying an aliquot to a POROS R2/H column. Alternatively, an immunological dot blot was performed for the qualitative identification of EPO-containing fractions.

Fractions containing EPO (10–15 ml) were pooled and applied to a hydroxyapatite column.

The yield of the butyl sepharose column was about 130 μg EPO (corresponds to about 85%). In general, the yield of the butyl sepharose was between 60 and 85% of the amount applied from the blue sepharose pool.

3. Hydroxyapatite Column

A 5 ml hydroxyapatite column (Econo-Pac CHT II ready-to-use column from BioRAD) was balanced with at least 5 CV of buffer F (20 mM Tris-HCl, pH 7.0; 2 M NaCl; 20% isopropanol) and then the butyl sepharose pool containing EPO from 2. (approx. 125 μg EPO) was drawn up at a flow of 0.5 ml/min.

The column was washed with at least 5 CV of buffer G (20 mM Tris-HCl, pH 7.0; 2 M NaCl) at 0.5 ml/min. The washing success was followed by measuring the protein content at OD280.

The elution of EPO was performed with buffer H (10 mM sodium phosphate, pH 7.0; 80 mM NaCl) at a flow of 0.5 ml/min. The elution solution was collected in 1–2 ml fractions.

The EPO content of the fractions, wash solutions and flow was determined through RP-HPLC by applying an aliquot to POROS R2/H column.

Fractions containing EPO (3–6 ml) were pooled. The yield of the hydroxyapatite column was about 80 μg of EPO (corresponds to about 60%). In general, the yield of the hydroxyapatite column amounted to between 50 and 65% of the butyl sepharose pool applied.

4. Concentration

The pooled EPO fractions from the hydroxyapatite step were concentrated by centrifugation through, e.g., Microsep by Filtron having an excusionsize of 10 kD; the concentration was adjusted to 0.1–0.5 mg/ml with 0.01% of Tween 20 and stored in aliquots at −20° C.

Table of Yields

|  | EPO (μg) | Yield (%) |
|---|---|---|
| Start | 245 | 100 |
| Blue sepharose | 175 | 70 |
| Butyl sepharose column | 130 | 53 |
| Hydroxyapatite column | 80 | 33 |
| Concentration | 60 | 25 |

The purity of the isolated EPO was approximately >90%, and even >95%, as a rule.

To increase the EPO yield, Method 2 was also used, in which the butyl sepharose step was missing. This method is applicable especially in the case of cell culture supernatants with or without 1% (v/v) FCS added, and delivers isolated EPO of approximately equal purity (90–95%). The presence of 5 mM $CaCl_2$ in the balancing buffer (buffer F) for the hydroxyapatite column led in this method to improved binding and thus also to a reproducible elution behavior of EPO in the hydroxyapatite step. Therefore Method 2 was practiced with basically the same procedure as in Method 1, with the following buffers:

1. Blue Sepharose Column:

| | |
|---|---|
| Balancing buffer (buffer A) | 20 mM Tris-HCl, pH 7.0 |
| | 5 mM $CaCl_2$; 100 mM NaCl |
| Washing buffer 1 (buffer B) | 20 mM Tris-HCl, pH 7.0 |
| | 5 mM $CaCl_2$; 250 mM NaCl |
| Washing buffer 2 (buffer C) | 20 mM Tris-HCl, pH 7.0 |
| | 5 mM $CaCl_2$, 250 mM NaCl |
| Elution buffer (buffer D) | 100 mM Tris-HCl, pH 7.0 |
| | 5 mM $CaCl_2$; 2 M NaCl |

2. Hydroxyapatite Column:

| | |
|---|---|
| Balancing buffer (buffer F) | 50 mM Tris-HCl, pH 7.0 |
| | 5 mM $CaCl_2$, 1 M NaCl |
| Washing buffer (buffer G) | 10 mM Tris-HCl, pH 7.0 |
| | 5 mM $CaCl_2$; 80 mM NaCl |
| Elution buffer (buffer H): | 10 mM sodium phosphate, pH 7.0 |
| | 0.5 mM $CaCl_2$; 80 mM NaCl |

Table of Yields

|  | EPO (μg) | Yield (%) |
|---|---|---|
| Start | 600 | 100 |
| Blue Sepharose | 450 | 75 |
| Hydroxyapatite column | 335 | 55 |
| Concentration | 310 | 52 |

The addition of 5 mM $CaCl_2$ to the buffers B to G in Method 1 also resulted in better binding and more definite elution of the hydroxyapatite column.

Example 10

Determination of the Specific Activity in vivo of EPO from Human Cell Lines (Bioassay on the Normocythemic Mouse)

The dose-related activity of EPO on the proliferation and differentiation of erythrocyte precursor cells was determined in vivo in mice based on the increase of reticulocytes in the blood after EPO administration.

For this purpose eight mice were treated parenterally in each essay with different doses of the EPO sample to be analyzed and of an EPO standard (balanced against the WHO's standard EPO). The mice were then kept under constant, defined conditions. 4 days after the EPO treatment, blood was taken from the mice and the reticulocytes stained with acridine orange. Determination of the number of reticulocytes per 30,000 erythrocytes was performed by microfluorimetry in a flow cytometer by analyzing the red fluorescence histogram.

The computation of the biological activity was made from the values of the reticulocyte counts of the specimen and those of the standard at the various doses by the method described by Linder of paired content determination with parallel straight lines (A. Linder, Planen und Auswerten von Versuchen, 3rd ed., 1969, Birkenhäuser Verlag Basel).

Result

| EPO from cell line | Specific Activity U/mg |
|---|---|
| HeLa S3 (Sample 1) | 100,000 |
| HeLa S3 (Sample 2) | 110,000 |

What is claimed is:

1. An isolated human cell, which contains a copy of an endogenous EPO gene in operable linkage with a heterologous promoter active in the human cell and produces at least 200 ng EPO/$10^6$ cells/24 h and wherein said endogenous EPO gene is not amplified and wherein the EPO gene has a signal peptide-coding sequence which codes for a signal peptide sequence wherein the sequence of the first 4 amino acids of said signal-peptide sequence is:

$$\text{Met-}X_1\text{-}X_2\text{-}X_3$$

wherein $X_1$ is Gly or Ser, $X_2$ is Ala, Val, Leu, Ile, Ser or Pro, and $X_3$ is Pro, Arg, Cys or His, provided that $X_1$-$X_2$-$X_3$ is not the sequence Gly-Val-His.

2. The isolated human cell according to claim 1, which produces 200–3000 ng EPO/$10^6$ cells/24 h.

3. The isolated human cell produced by gene amplification from a cell according to claim 1, which contains several copies of an endogenous EPO gene, each in operative linkage with a heterologous promoter active in the human cell and produces at least 1000 ng EPO/$10^6$ cells/24 h.

4. The isolated human cell according to claim 3, which produces 1000–25,000 ng EPO/$10^6$ cells/24 h.

5. The isolated human cell according to claim 1 which it is an immortalized cell.

6. The isolated human cell according to claim 1, which can be cultured in serum-free medium.

7. The isolated human cell according to claim 1, which is selected from an HT 1080 cell, an HeLa S3 cell, or a Namalwa cell.

8. Human cell according to claim 1, wherein the activated endogenous EPO gene is under control of a viral promoter.

9. The isolated human cell according to claim 8, wherein the viral promoter is CMV promoter.

10. Human cell according to claim 1, wherein the amino acid sequence of the first 4 amino acids are:

(a) Met-Gly-Ala-His, SEQ ID NO: 8
(b) Met-Ser-Ala-His, SEQ ID NO: 10
(c) Met-Gly-Val-Pro, SEQ ID NO: 12 or
(d) Met-Ser-Val-His, SEQ ID NO: 14.

11. The isolated human cell according to claim 1, wherein the sequence of the first 4 amino acids of the signal peptide is Met-Ser-Ala-His SEQ ID NO: 10.

12. A method for the preparation of a human EPO-producing cell producing at least 200 ng EPO/$10^6$ cells/24 h, comprising the steps:

(a) preparation of human starting cells which contain at least one copy of an endogenous EPO gene,
(b) transfection of the cells with a DNA construct comprising:

(i) two flanking DNA sequences which are homologous to regions of the human EPO gene locus, to permit homologous recombination,
(ii) a signal peptide-coding sequence which codes for a signal peptide sequence wherein the sequence of the first 4 amino acids of said signal-peptide coding sequence is:

$$\text{Met-}X_1\text{-}X_2\text{-}X_3$$

wherein $X_1$ is Gly or Ser, $X_2$ is Ala, Val, Leu, Ile, Ser or Pro, and $X_3$ is Pro, Arg, Cys or His, provided that $X_1$-$X_2$-$X_3$ is not the sequence Gly-Val-His,
(iii) a positive selection marker gene, and
(iv) a heterologous expression control sequence which is active in the human cell, (c) culturing the transfected cells under conditions in which a selection takes place for the presence of the positive selection marker gene,
(d) analyzing the cells selected according to step (c), and
(e) identification of the EPO-producing cells producing at least 200 ng/$10^6$ cells/24 h, wherein the EPO gene is not amplified.

13. The method according to claim 12, wherein the homologous DNA sequences are selected from the region of the 5'-untranslated sequences, exon 1 and intron 1 of the EPO gene.

14. The method according to claim 13, wherein at least one of the DNA sequences which are homologous to regions of the human EPO gene site has a modified exon 1.

15. The method according to claim 13, wherein the selection marker gene is a neomycin phosphotransferase gene.

16. The method according to claim 13 wherein the DNA construct additionally comprises an amplification gene.

17. The method according to claim 16, wherein the amplification gene is a dihydrofolate reductase gene.

18. Method according to claim 17, wherein the amplification gene is a dihydrofolate reductase arginine-mutant.

19. The method for the preparation of a human EPO-producing cell according to claim 3 comprising the steps:

(a) amplification of the EPO gene in the cell line of claim 1,
(b) harvesting of EPO-producing cells which contain several copies of the endogenous EPO gene each in operable linkage with a heterologous expression control sequence.

20. The method according to claim 12 wherein the expression control sequence is a CMV promoter/enhancer.

21. The isolated human cell according to claim 1, wherein the EPO gene has a signal peptide-coding sequence which is different from the natural signal peptide-coding sequence.

22. A method for the preparation of a human EPO-producing cell producing at least 200 ng EPO/$10^6$ cells/24 h, comprising the steps:
 (a) preparation of human starting cells which contain at least one copy of an endogenous EPO gene,
 (b) transfection of the human starting cells with plasmid p189 (DSM 1161) in linearized form,
 (c) culturing the transfected cells under conditions in which a selection takes place for the presence of the positive selection marker gene,
 (d) analyzing the cells selected according to step (c), and
 (e) identification of the EPO-producing cells producing at least 200 ng/$10^6$ cells/24 h, wherein the EPO gene is not amplified.

* * * * *